(12) United States Patent
Yu et al.

(10) Patent No.: US 12,030,048 B2
(45) Date of Patent: Jul. 9, 2024

(54) MICROFLUIDIC CHIP

(71) Applicant: SHENZHEN BIORAIN TECHNOLOGY CO., LTD., Guangdong (CN)

(72) Inventors: Linfen Yu, Guangdong (CN); Wei Yang, Guangdong (CN)

(73) Assignee: SHENZHEN BIORAIN TECHNOLOGY CO., LTD., Shenzhen (CN)

(*) Notice: Subject to any disclaimer, the term of this patent is extended or adjusted under 35 U.S.C. 154(b) by 713 days.

(21) Appl. No.: 17/292,716

(22) PCT Filed: Mar. 6, 2019

(86) PCT No.: PCT/CN2019/077082
§ 371 (c)(1),
(2) Date: May 10, 2021

(87) PCT Pub. No.: WO2020/177088
PCT Pub. Date: Sep. 10, 2020

(65) Prior Publication Data
US 2022/0001381 A1    Jan. 6, 2022

(30) Foreign Application Priority Data

Mar. 1, 2019 (CN) .......................... 201910158935.5

(51) Int. Cl.
*B01L 3/00* (2006.01)
*B01F 23/00* (2022.01)
(Continued)

(52) U.S. Cl.
CPC ..... *B01L 3/50273* (2013.01); *B01L 3/502715* (2013.01); *B01L 3/502753* (2013.01);
(Continued)

(58) Field of Classification Search
CPC .......... B01L 3/50273; B01L 3/502715; B01L 3/502753; B01L 3/502784;
(Continued)

(56) References Cited

FOREIGN PATENT DOCUMENTS

| CN | 105498875 A | 4/2016 |
| CN | 107233936 A | 10/2017 |

(Continued)

OTHER PUBLICATIONS

International Search Report of PCT Patent Application No. PCT/CN2019/077082 issued on Dec. 4, 2019.

*Primary Examiner* — Jennifer Wecker
*Assistant Examiner* — Oyeleye Alexander Alabi

(57) ABSTRACT

Disclosed is a microfluidic chip, including a chip upper cover, a chip lower layer, a membrane, a sealing gasket and a sealing ring. The microfluidic chip is provided with a sample storage zone, a droplet formation zone, a droplet storage zone, a droplet detection zone and a waste liquid storage zone. The sample storage zone, the droplet formation zone, the droplet storage zone, the droplet detection zone and the waste liquid storage zone communicate by means of a micropore or a micro-channel. The droplet formation zone is used to transform the sample phase into tens of thousands to millions of droplets, the droplets undergo the PCR reaction in the droplet storage zone, the droplet detection zone is used to perform optical detection on the droplets after PCR reaction, and the waste liquid storage zone is used to collect and store the detected droplets and continuous phase.

11 Claims, 8 Drawing Sheets

(51) Int. Cl.
| | |
|---|---|
| *B01F 23/41* | (2022.01) |
| *B01F 101/23* | (2022.01) |
| *B23Q 17/24* | (2006.01) |
| *C12M 1/34* | (2006.01) |
| *C12Q 1/04* | (2006.01) |
| *C12Q 1/18* | (2006.01) |
| *C12Q 1/686* | (2018.01) |
| *G01N 21/3577* | (2014.01) |
| *G01N 21/359* | (2014.01) |
| *G01N 21/39* | (2006.01) |
| *G01N 21/45* | (2006.01) |
| *G01N 21/64* | (2006.01) |
| *G01N 30/12* | (2006.01) |
| *G01N 30/68* | (2006.01) |
| *G01N 30/70* | (2006.01) |
| *G01N 30/72* | (2006.01) |
| *G01N 30/88* | (2006.01) |
| *G01N 33/00* | (2006.01) |
| *G01N 33/18* | (2006.01) |
| *G01N 33/50* | (2006.01) |
| *G01N 33/68* | (2006.01) |

(52) U.S. Cl.
CPC . *B01L 3/502784* (2013.01); *B01L 2200/0684* (2013.01); *B01L 2200/0689* (2013.01); *B01L 2300/04* (2013.01); *B01L 2300/0627* (2013.01); *B01L 2300/0681* (2013.01); *C12Q 1/686* (2013.01)

(58) Field of Classification Search
CPC ..... B01L 2200/0684; B01L 2200/0689; B01L 2300/04; B01L 2300/0627; B01L 2300/0681; B01L 3/5025; B01L 2200/027; B01L 2400/086; B01L 2200/10; B01L 7/5255; B01L 3/5027; B01L 3/502792; B01L 2200/0621; B01L 2300/0829; B01L 2300/0861; B01L 2300/0887; B01L 2300/185; C12Q 1/686; C12Q 1/6851
See application file for complete search history.

(56) References Cited

FOREIGN PATENT DOCUMENTS

| CN | 107442191 A | 12/2017 | |
|---|---|---|---|
| CN | 109351368 A | * 2/2019 | ............ B01L 3/5027 |

* cited by examiner

MICROFLUIDIC CHIP

TECHNICAL FIELD

The application relates to the technical field of digital PCR, in particular to a microfluidic chip.

BACKGROUND

Most of the existing microdroplet digital PCR systems adopt the split-type technical route, i.e., droplet formation, PCR reaction and droplet detection are respectively completed on different instruments. The operation steps of the technical route are cumbersome, and whole-process closed operation is difficult to achieve, so that the technical route fails to meet the requirements for clinical diagnosis and analysis, and restricts the clinical application of the technology.

SUMMARY

The application provides a microfluidic chip, used for implementing the whole-process operation steps, such as sample storage and transfer, droplet formation, droplet storage, PCR thermal cycling and droplet detection.

The microfluidic chip of the application includes a chip upper cover, a chip lower layer, a membrane, a sealing gasket and a sealing ring; the lower surface of the chip upper cover fits to the upper surface of the chip lower layer, and the lower surface of the chip lower layer fits to the upper surface of the membrane. Adhesion, welding, bonding and other methods are adopted for fitting to ensure firm and tight fitting.

Preferably, the microfluidic chip of the application is functionally divided into a sample storage zone, a droplet formation zone, a droplet storage zone, a droplet detection zone and a waste liquid storage zone. The sample storage zone and the waste liquid storage zone are arranged on the lower surface of the chip upper cover, and the droplet formation zone, the droplet storage zone and the droplet detection zone are arranged on the lower surface of the chip lower layer. Communication between the sample storage zone and the droplet formation zone, communication between the droplet formation zone and the droplet storage zone, communication between the droplet storage zone and the droplet detection zone, and communication between the droplet detection zone and the waste liquid storage zone are all realized by means of a micro-channel or a micropore.

Preferably, the sample storage zone is used for storing the sample phase; the droplet formation zone is used for transforming the sample phase into tens of thousands to millions of droplets, e.g., transforming the aqueous-phase sample into water-in-oil droplets. The droplets undergo the PCR reaction in the droplet storage zone. After the PCR reaction, the droplet detection zone is used to perform optical detection on the droplets after PCR reaction. The waste liquid storage zone is used to collect and store the detected droplets and continuous phase.

Preferably, the microfluidic chip of the application is provided with several independently and abreast arranged sets of sample storage zones, droplet formation zones, droplet storage zones, droplet detection zones and waste liquid storage zones, which correspond to several samples. Each set of sample storage zone, droplet formation zone, droplet storage zone, droplet detection zone and waste liquid storage zone forms a whole-process processing path for one sample, and the microfluidic chip can independently perform the sample storage, droplet formation, the droplet storage, the PCR thermal cycling, the droplet detection and the waste liquid storage on the several samples.

Preferably, the microfluidic chip of the application is horizontally placed during sample loading, and vertically or obliquely placed during the subsequent droplet formation, PCR reaction and droplet detection, wherein the droplet formation zone is located at the lower end of the microfluidic chip, and the waste liquid storage zone is located at the upper end of the microfluidic chip. The microfluidic chip placed vertically or obliquely at a certain angle allows rapid up-floating of the droplets to avoid affecting the subsequent process of droplet formation, and ensures the smooth and lossless transfer of the droplets in the detection process.

Preferably, the chip upper cover is provided with a sample injection orifice, a sealing gasket mounting hole, an exhaust hole and a window penetrating through the upper surface and the lower surface of the chip upper cover. The window allows the light get through, so that the droplets can be conveniently detected by optical detection equipment. The upper surface of the chip upper cover is provided with a sample loading column, and the sample injection orifice is arranged at the center of the sample loading column. The lower surface of the chip upper cover is provided with a sample loading micro-channel, a sample storage pool, an exhaust channel and a waste liquid storage pool, the sample injection orifice is connected with the sample storage pool by means of the sample loading micro-channel, and the waste liquid storage pool is connected with the exhaust hole by means of the exhaust channel.

Preferably, the sealing gasket is symmetrically provided with formation continuous phase injection orifices and detection continuous phase injection orifices alternately, i.e., two orifices at two ends of the sealing gasket are formation continuous phase injection orifices, orifices adjacent thereto are detection continuous phase injection orifices, and then in turn, orifices are formation continuous phase injection orifices, in such a way, the formation continuous phase injection orifices and the detection continuous phase injection orifices are symmetrically and alternately arranged at the two ends. The formation continuous phase injection orifice is connected with the detection continuous phase injection orifice by means of a connecting section. The upper ends and the lower ends of the formation continuous phase injection orifice and the detection continuous phase injection orifice are each provided with an annular seal, and the annular seal is of a single-ring structure or a multi-ring structure.

Preferably, the sealing ring includes circular rings connected by connecting sections, the upper end and the lower end of the circular ring are each provided with a single-ring annular seal or a multi-ring annular seal, and an inner wall of the circular ring sleeves the sample loading column.

Preferably, the thickness of the membrane is less than 1 mm. The membrane should be as thin as possible to accelerate the heat transfer during the PCR reaction. The membrane is used to seal the orifice, the channel and the droplet storage zone on the lower surface of the chip lower layer, and plays a role in transferring heat with the droplet storage zone.

Preferably, the droplet storage zone is provided with a droplet storage pool; when the microfluidic chip is vertically placed, the upper end of the droplet storage pool is in the shape of sharp corner, and the tip of the sharp corner communicates to the droplet detection zone to ensure rapid and lossless transfer of the droplets.

Preferably, the droplet formation zone includes a formation continuous phase inlet, a formation continuous phase channel communicating with the formation continuous phase inlet, a sample inlet and a sample channel communicating with the sample inlet. Wherein the formation continuous phase inlet communicates with the formation continuous phase injection orifice of the sealing gasket; and the sample channel is connected with at least one sample branching channel, and the sample branching channel is connected with the droplet storage pool by means of a horn mouth. For droplet formation, a certain volume of the formation continuous phase is injected into the droplet storage pool, and the sample phase enters the droplet storage pool through the sample branching channel to form the droplets at the horn mouth, and then the droplets enter the droplet storage pool. The formation continuous phase is mainly used to facilitate the droplet formation, and the detection continuous phase is mainly used to push the droplets.

Preferably, the formation continuous phase channel is provided with a formation continuous phase filtering zone, and the sample channel is provided with a sample filtering zone. Micro-columns are densely arranged at a distance of 10 μm to 100 μm in the sample phase filtering zone and the formation continuous phase filtering zone, respectively, and the densely arranged micro-columns are used for intercepting impurities. The horn mouth is a bilaterally symmetrical opening in <shape or a single-bevel opening in ∠ shape, and the angle of the horn mouth ranges from 5 degrees to 120 degrees. The number of the sample phase branching channels preferably ranges from 1 to 40.

Preferably, the depth of the droplet storage pool is greater than or equal to twice the depth of the horn mouth, the depth of the droplet storage pool is greater than or equal to twice the depth of the sample phase branching channel, and the depth of the horn mouth is the same as that of the sample phase branching channel.

Preferably, a width-depth ratio of the sample phase branching channel is greater than or equal to 1, the width of the sample phase branching channel ranges from 10 μm to 200 μm, the depth of the sample phase branching channel ranges from 2 μm to 100 μm, and the depth of the droplet storage pool is greater than 50 μm.

Preferably, the droplet detection zone includes a detection continuous phase inlet, a detection continuous phase channel communicating with the detection continuous phase inlet, a droplet inlet, a droplet channel communicating with the droplet inlet and a detection channel. Wherein the detection continuous phase inlet communicates with the detection continuous phase injection orifice of the sealing gasket; and the detection continuous phase channel is provided with a detection continuous phase filtering zone, and micro-columns are densely arranged at a distance of 10 μm to 100 μm in the detection continuous phase filtering zone. The densely arranged micro-columns are used for intercepting impurities. The detection continuous phase channel merges into the droplet channel to connect with the detection channel, the detection channel communicates with a waste liquid channel, and the waste liquid channel is connected with a waste liquid outlet. The width of the detection channel is 1-1.5 times the droplet diameter, and the depth of the detection channel is 1-1.5 times the droplet diameter.

Preferably, the sample storage zone includes the sample loading micro-channel, the sample storage pool and a sample outlet, and the lower end of the sample storage pool is in the oblique shape; and the sample outlet is arranged at the bottom sharp corner of the sample storage pool, and the sample outlet communicates with the sample inlet of the droplet formation zone. The waste liquid storage zone includes the exhaust channel and the waste liquid storage pool, and the waste liquid storage pool is connected with the exhaust hole by means of the exhaust channel.

Preferably, the sample phase is aqueous phase, the formation continuous phase and the detection continuous phase are oil phase, and the droplet is preferably a water-in-oil droplet.

The microfluidic chip of the application is horizontally placed during the sample loading, and the sample phase enters the sample storage zone. Subsequently, the microfluidic chip is vertically or obliquely placed, with the droplet formation zone located at the lower end and the waste liquid storage zone located at the upper end, and the sample in the sample storage zone is driven to the droplet formation zone by external pressure. The droplet formation zone disperses the sample phase into tens of thousands to millions of droplets, and the droplets are stored in the droplet storage zone. The PCR thermal cycling can be conducted on the droplets in the droplet storage zone in combination with external temperature-controlled equipment. After the PCR reaction, the droplets enter the droplet detection zone for individual detection with the optical signal. The detected droplets are stored in a waste liquid storage pool of the waste liquid storage zone.

The microfluidic chip of the application integrates the whole-process operation steps of droplet digital PCR, such as the droplet formation, the droplet storage, the PCR thermal cycling and the droplet detection, thereby significantly reducing manual operation, reducing the operation difficulty, meeting the requirement for automatic clinical detection, and being capable of simultaneously processing a plurality of independent samples to obviously improve the detection efficiency.

BRIEF DESCRIPTION OF THE DRAWINGS

In order to illustrate the technical solutions of the application more clearly, figures used in the embodiments will be introduced below briefly. It should be understood that the figures described below only show some embodiments of the application. Those of ordinary skill in the art can also obtain other figures based on those figures without creative work.

Figure 1:
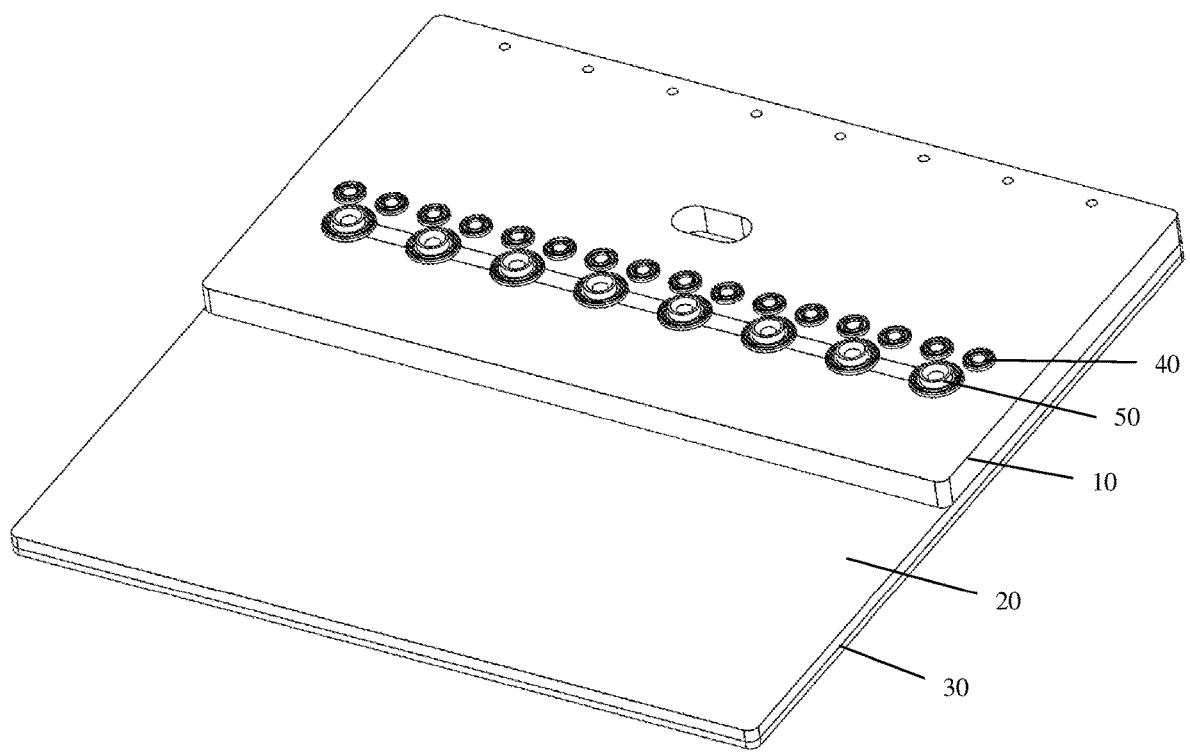
FIG. 1 is a schematic diagram of a microfluidic chip according to the application.

Reference numbers in the figures are as follows: 10. chip upper cover; 20. chip lower layer; 30. membrane; 40. sealing gasket; 50. sealing ring; 60. droplet formation zone; 70. droplet storage zone; 80. droplet detection zone; 90. waste liquid storage zone; 100. sample storage zone; 11. upper surface of chip upper cover; 12. lower surface of chip upper cover; 13. sample loading column; 131. sample injection orifice; 14. sealing gasket mounting hole; 15. exhaust hole; 16. window; 21. upper surface of chip lower layer; 22. lower surface of chip lower layer; 31. upper surface of membrane; 32. lower surface of membrane; 41. formation continuous phase injection orifice; 42. detection continuous phase injection orifice; 43. first annular seal; 44. connecting section; 51. inner wall; 52. second annular seal; 61. sample phase inlet; 62. sample phase filtering zone; 621. micro-column; 63. sample phase channel; 631. sample phase branching channel; 632. horn mouth; 64. formation continuous phase inlet; 65. formation continuous phase filtering zone; 66. formation continuous phase channel; 71. droplet storage pool; 81. detection continuous phase inlet; 82. detection continuous phase filtering zone; 83. detection continuous phase channel; 84. droplet inlet; 85. droplet channel; 86. detection channel; 87. waste liquid channel; 88. waste liquid outlet; 91. exhaust channel; 92. waste liquid storage pool; 101. sample loading micro-channel; 102. sample storage pool; 103. sample outlet.

DETAILED DESCRIPTION OF THE PREFERRED EMBODIMENTS

Technical solutions in the embodiments of the application will be described clearly and completely in combination with figures in the embodiments of the application. Obviously, the described embodiments are only part, but not all, of the embodiments of the application. Based on the embodiments of the application, all other embodiments obtained by those of ordinary skill in the art without creative work fall within the protection scope of the application.

Referring to FIG. 1 to FIG. 14, the application provides a microfluidic chip, used for implementing the whole-process operation steps, such as sample storage and transfer, droplet formation, droplet storage, PCR thermal cycling and droplet detection. Wherein, after sample loading, a sample phase is stored in a sample storage zone 100, the droplet formation is completed in a droplet formation zone 60, the droplet storage and the PCR thermal cycling are completed in a droplet storage zone 70, the droplet detection is completed in a droplet detection zone 80, and waste liquid obtained after the droplet detection is collected in a waste liquid storage zone 90.

In the embodiment, the microfluidic chip of the application is provided with eight independently and abreast arranged sets of droplet formation zones 60, droplet storage zones 70, droplet detection zones 80, waste liquid storage zones 90 and sample storage zones 100, which correspond to eight samples, i.e., each set of sample storage zone 100, droplet formation zone 60, droplet storage zone 70, droplet detection zone 80 and waste liquid storage zone 90 forms a whole-process processing path for one sample. The microfluidic chip of the application can simultaneously and independently perform the droplet formation, the droplet storage, the PCR thermal cycling, the droplet detection and other operations on the eight samples. The following description mainly illustrates the whole-process processing path for a single sample. Obviously, the whole-process processing paths for all samples share the same principle and structure.

The microfluidic chip of the application includes a chip upper cover 10, a chip lower layer 20, a membrane 30, a sealing gasket 40 and a sealing ring 50. Wherein, the waste liquid storage zone 90 and the sample storage zone 100 are arranged on the chip upper cover 10, and the droplet formation zone 60, the droplet storage zone 70 and the droplet detection zone 80 are arranged on the chip lower layer 20. Communication between the sample storage zone 100 and the droplet formation zone 60, communication between the droplet formation zone 60 and the droplet storage zone 70, communication between the droplet storage zone 70 and the droplet detection zone 80, and communication between the droplet detection zone 80 and the waste liquid storage zone 90 are all realized by means of a micro-channel or a micropore.

The sample storage zone 100 is used to temporarily store the sample phase loaded. The microfluidic chip is horizontally placed during the sample loading, and the sample phase enters a sample storage pool 102 of the sample storage zone 100 through a sample injection orifice 131. Subsequently, the microfluidic chip is vertically or obliquely placed, with the droplet formation zone 60 located at the lower end and the waste liquid storage zone 90 located at the upper end, and the sample in the sample storage zone 100 is driven to the droplet formation zone 60 by external pressure.

In the embodiment, the droplet formation zone 60 is used to disperse the aqueous-phase sample into tens of thousands to millions of water-in-oil droplets, and the water-in-oil droplets are stored in the droplet storage zone 70. The PCR thermal cycling can be conducted on the water-in-oil droplets in the droplet storage zone 70 in combination with external temperature-controlled equipment. After the PCR reaction, the droplets enter the droplet detection zone 80 for individual detection with the optical signal. The detected droplets are stored in a waste liquid storage pool 93 of the waste liquid storage zone 90.

The chip upper cover 10 includes an upper surface 11 of the chip upper cover and a lower surface 12 of the chip upper cover, the chip lower layer 20 includes an upper surface 21 of the chip lower layer and a lower surface 22 of the chip lower layer, and the membrane 30 includes an upper surface 31 of the membrane and a lower surface 32 of the membrane. The lower surface 12 of the chip upper cover fits to the upper surface 21 of the chip lower layer, and the lower surface 22 of the chip lower layer fits to the upper surface 31 of the membrane. Adhesion, welding, bonding and other methods are adopted for fitting to ensure firm and tight fitting.

Figure 5:
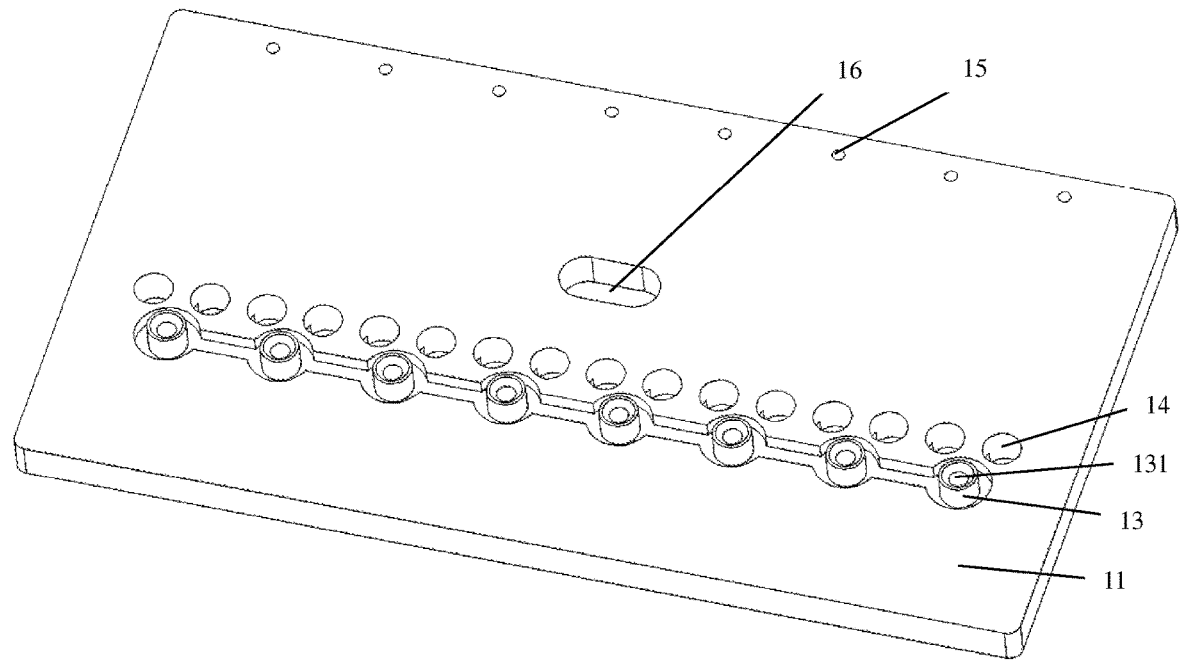
FIG. 5 is a schematic diagram of an upper surface of a chip upper cover of the microfluidic chip in FIG. 1.
Figure 6:
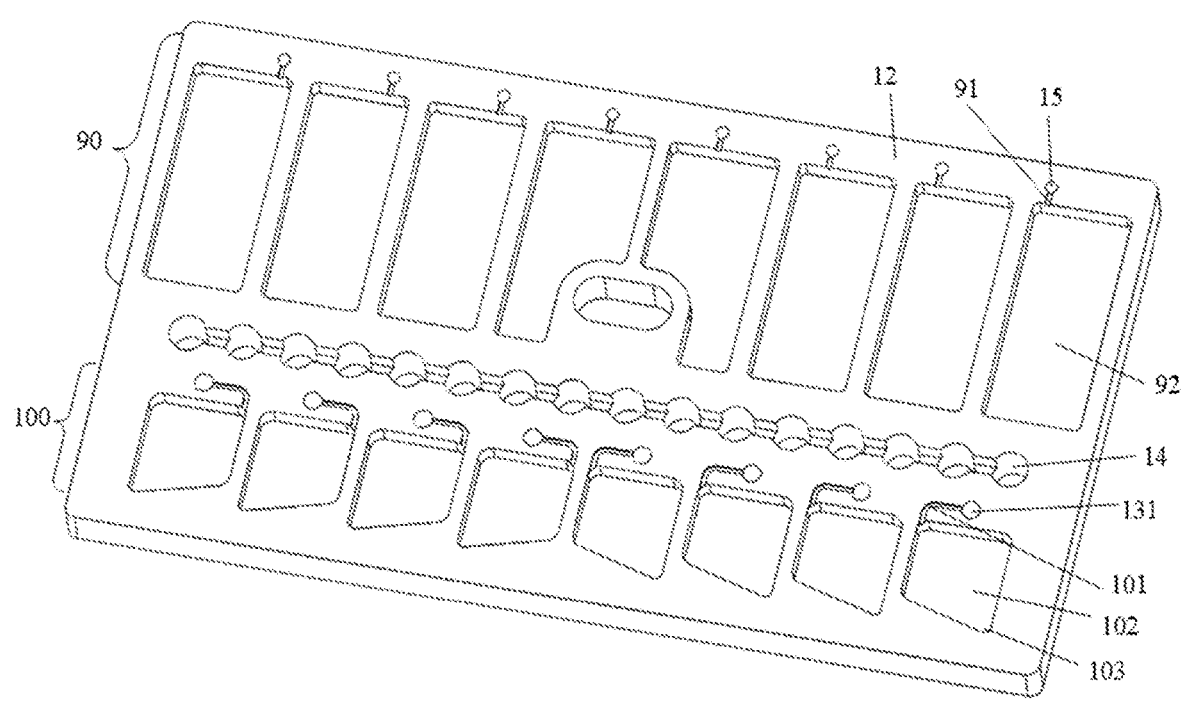
FIG. 6 is a schematic diagram of a lower surface of a chip upper cover of the microfluidic chip in FIG. 1.
Figure 7:
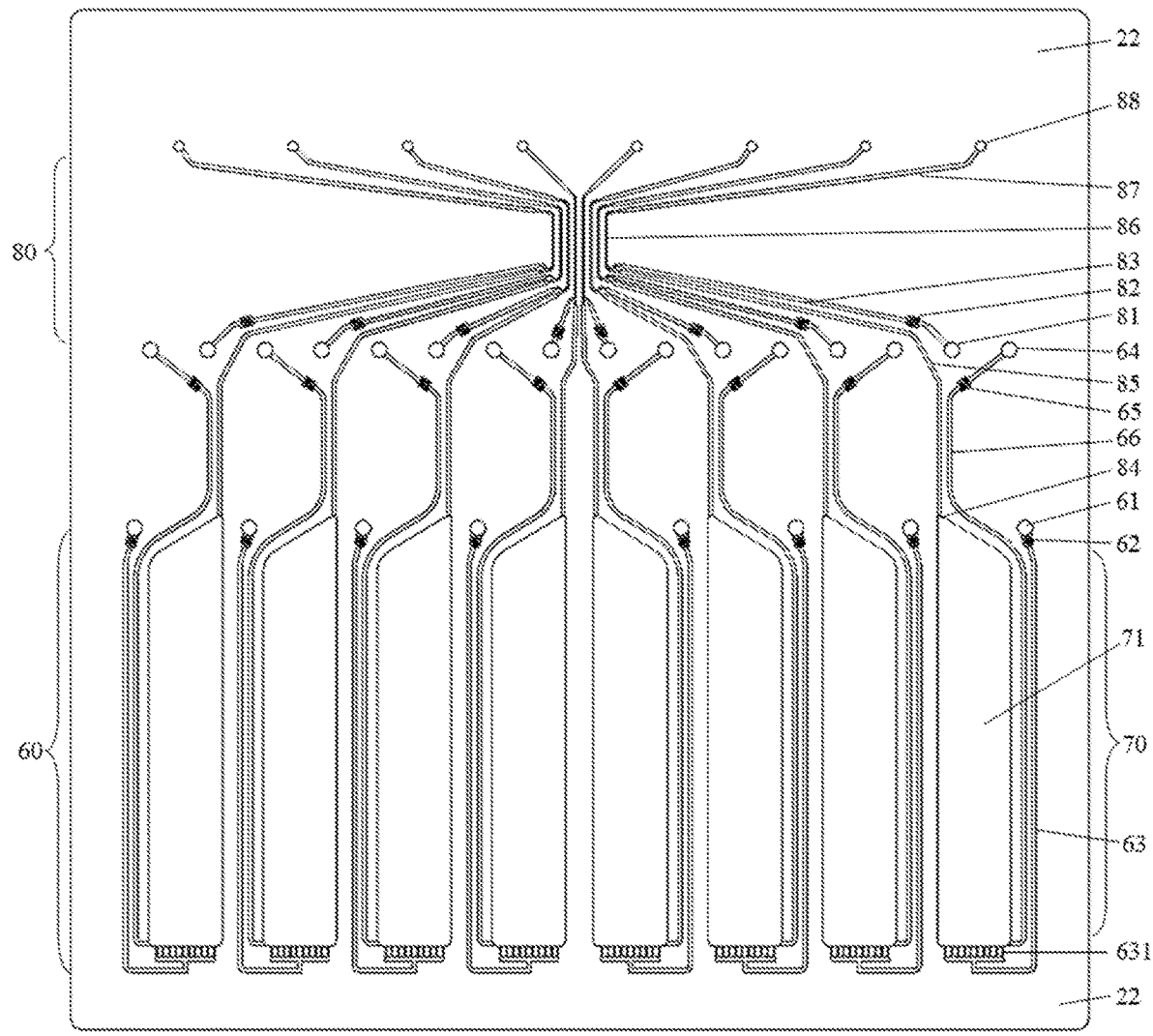
FIG. 7 is a schematic diagram of a lower surface of a chip lower layer of the microfluidic chip in FIG. 1.
Figure 8:
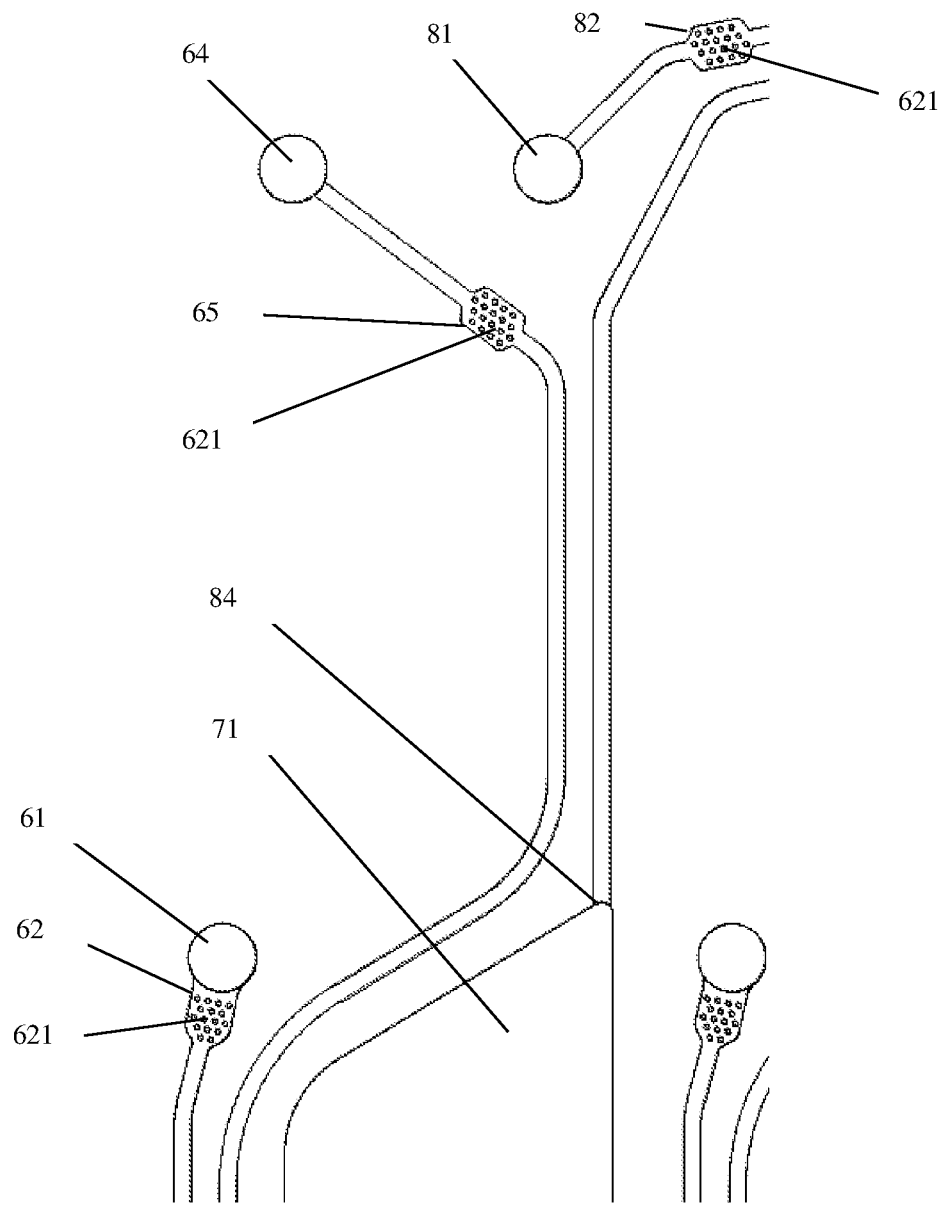
FIG. 8 is a partial enlarged view of the microfluidic chip in FIG. 1.
Figure 9:
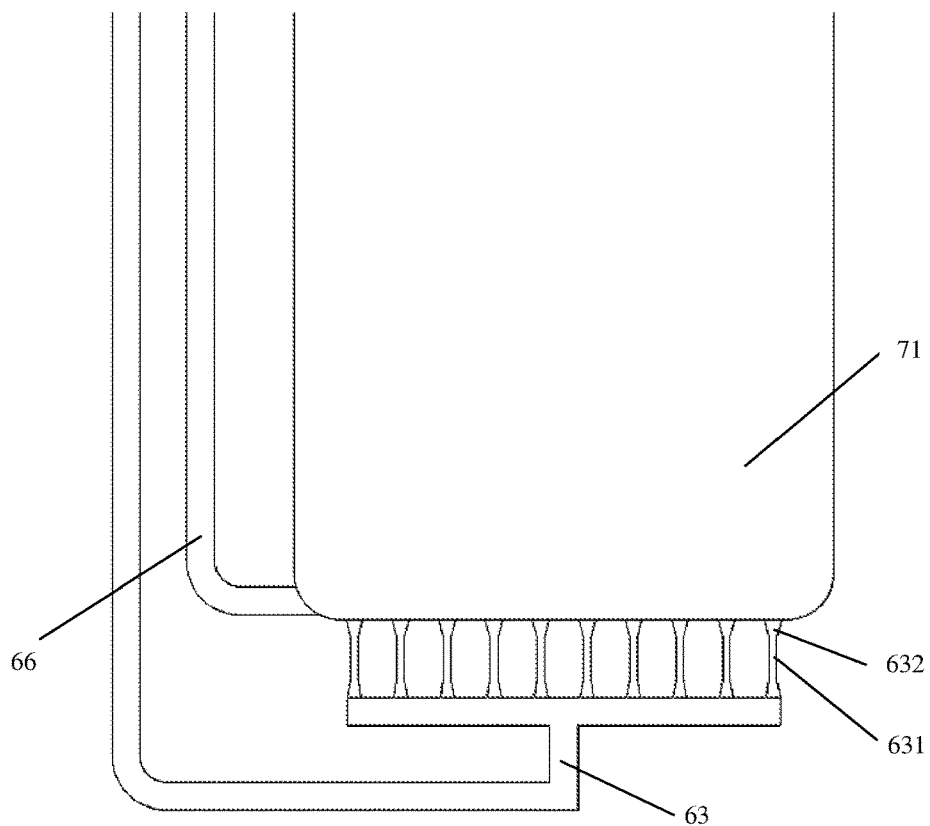
FIG. 9 is a partial enlarged view of a droplet formation zone of the microfluidic chip in FIG. 1.
Figure 10:
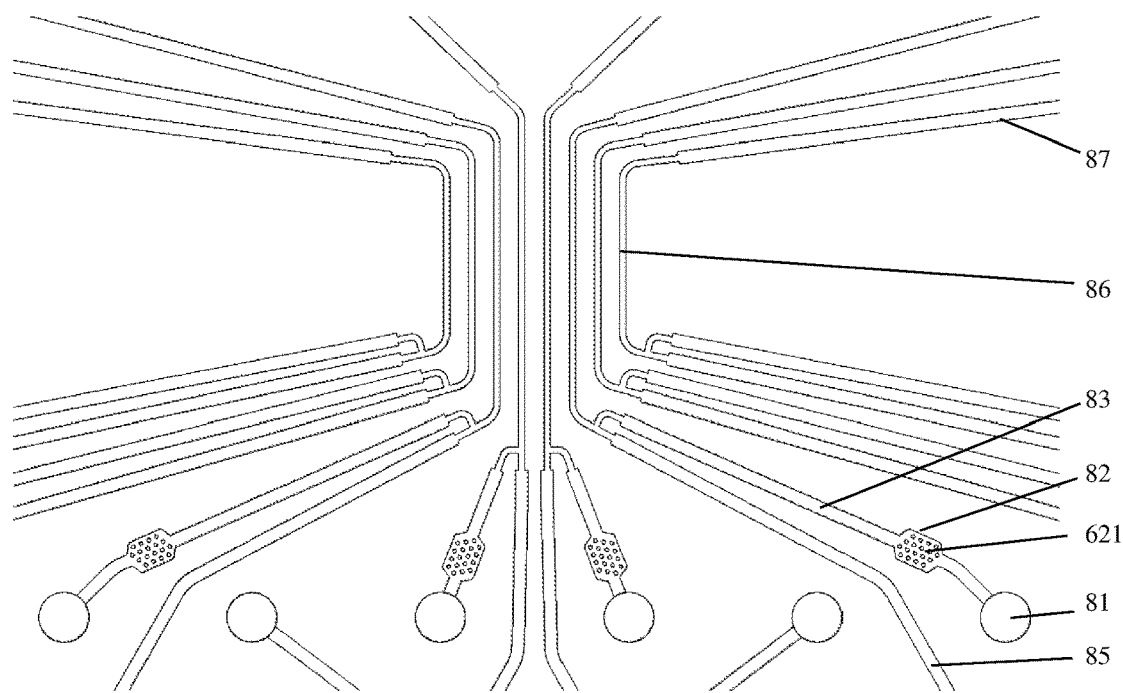
FIG. 10 is a partial enlarged view of a droplet detection zone of the microfluidic chip in FIG. 1.

As shown in FIG. 5 and FIG. 6, the sample storage zone 100 includes eight sets of sample loading micro-channels 101 and sample storage pools 102, and the waste liquid storage zone 90 includes eight sets of exhaust channels 91 and waste liquid storage pools 92. The chip upper cover 10 is provided with sample injection orifices 131, sealing gasket mounting holes 14, exhaust holes 15 and windows 16 penetrating through the upper surface and the lower surface of the chip upper cover 10. The upper surface 11 of the chip upper cover is provided with sample loading columns 13, and sample injection orifices 131 are arranged at the centers of the sample loading columns 13. The lower surface 12 of the chip upper cover is provided with the sample loading micro-channels 101, the sample storage pools 102, the exhaust channels 91 and the waste liquid storage pools 92, the sample injection orifices 131 are connected with the sample storage pools 102 by means of the sample loading micro-channels 101, and the waste liquid storage pools 92 are connected with the exhaust holes 15 by means of the exhaust channels 91. The windows 16 allow the light to get through, so that the droplets can be conveniently detected by optical detection equipment.

As shown in FIG. 7 to FIG. 10, the droplet formation zone 60, the droplet storage zone 70 and the droplet detection zone 80 are arranged on the lower surface 22 of the chip lower layer. The droplet formation zone 60 includes eight sets of sample phase inlets 61, sample phase filtering zones 62, micro-columns 621, sample phase channels 63, sample phase branching channels 631, horn mouths 632, formation continuous phase inlets 64, formation continuous phase filtering zones 65, micro-columns 621 and formation continuous phase channels 66. The droplet storage zone 70 includes eight droplet storage pools 71. The droplet detection zone 80 includes eight sets of detection continuous phase inlets 81, detection continuous phase filtering zones 82, micro-columns 621, detection continuous phase channels 83, droplet inlets 84, droplet channels 85, detection channels 86, waste liquid channels 87 and waste liquid outlets 88.

As shown in FIG. 7 to FIG. 10, the formation continuous phase enters from the formation continuous phase inlet 64, passes through the formation continuous phase filtering zone 65, and then enters the droplet storage pool 71 through the continuous phase channel 66. The sample phase enters from the sample phase inlet 61, passes through the sample filtering zone 62 and then enters the sample phase branching channel 631 through the sample phase channel 63. The sample phase branching channel 631 is connected with the droplet storage pool 71 by means of the horn mouth 632. The horn mouth 632 is a bilaterally symmetrical opening in <shape or a single-bevel opening in ∠ shape, and the angle of the horn mouth ranges from 5 degrees to 120 degrees, and the number of the sample phase branching channels 631 ranges from 1 to 40. The droplet formation efficiency increases with the increasing number of branching channels. When entering the droplet storage pool 71 storing the formation continuous phase by passing through the horn mouth 632, the sample phase is broken by means of a differential pressure and a surface tension to form individual droplets, and the droplets are covered by the formation continuous phase.

Further, the depth dimension of the horn mouth 632 is the same as that of the sample phase branching channel 631, and the depth dimension of the droplet storage pool 71 is greater than or equal to twice the depth dimension of the horn mouth 632. The width of the sample phase branching channel 631 is 10 μm to 200 μm and the depth thereof is 2 μm to 100 μm, and a width-depth ratio of the sample phase branching channel 631 is greater than or equal to 1. The depth of the droplet storage pool 71 is greater than 50 μm.

Micro-columns 621 are densely arranged at a distance of 10 μm to 100 μm in the sample phase filtering zone 62, the formation continuous phase filtering zone 65 and the detection continuous phase filtering zone 82, respectively, and the densely arranged micro-columns are used for intercepting impurities.

The detection continuous phase channel 83 merges into the droplet channel 85 to connect with the detection channel 86. The width and depth of the detection channel 86 are 1-1.5 times the droplet diameter. The detection continuous phase enters the detection continuous phase filtering zone 82 through the detection continuous phase inlet 81, and enters the detection continuous phase channel 83 after being filtered by the micro-columns 621. Meanwhile, the droplets enter the droplet channel 85 through the droplet inlet 84, and the droplets and the detection continuous phase enter the detection channel 86 together. The distance between the droplets increases with the intruded detection continuous phase, which is beneficial for detecting droplets by means of other optical detection systems.

In the embodiment, eight sets of detection channels 86 arranged in parallel is beneficial for detection by means of other optical detection systems. The detection channel 86 communicates with the waste liquid channel 87, thus the detected droplets and the detection continuous phase flow to the waste liquid outlet 88 through the waste liquid channel 87.

As shown in FIG. 2, FIG. 4, FIG. 7 and FIG. 9, the droplet storage pool 71 is arranged on the lower surface 22 of the chip lower layer, and fits to and is sealed by the membrane 30 to define a closed droplet storage space.

As shown in FIG. 2, FIG. 4, FIG. 5 and FIG. 6, the sample storage pool 102 and the waste liquid storage pool 92 are arranged on the lower surface 12 of the chip upper cover, and fit to and are sealed by the chip lower layer 21 to define a closed sample storage space and a closed waste liquid storage space respectively.

Figure 11:
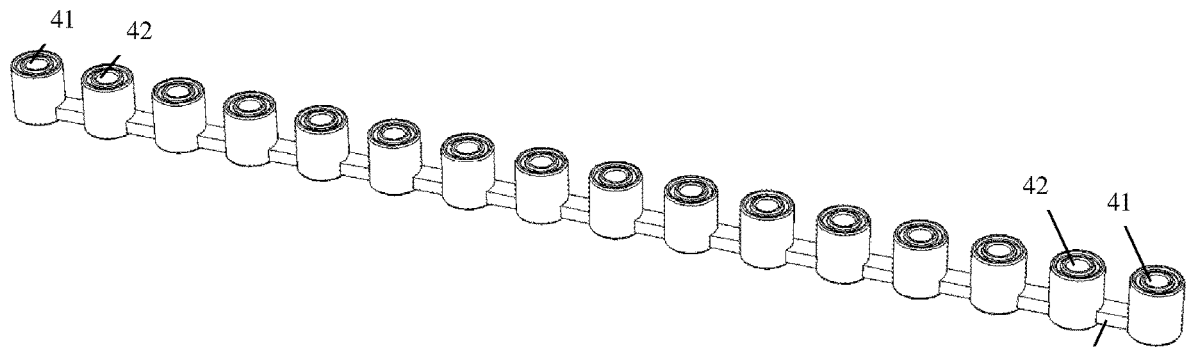
FIG. 11 is a schematic diagram of a sealing gasket of the microfluidic chip in FIG. 1.
Figure 12:
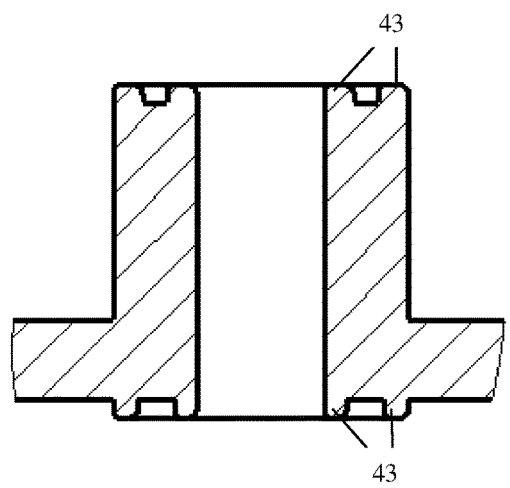
FIG. 12 is a sectional view of the sealing gasket of the microfluidic chip in FIG. 1.

As shown in FIG. 11 and FIG. 12, the sealing gasket 40 includes eight formation continuous phase injection orifices 41 and eight detection continuous phase injection orifices 42, which are connected by connecting sections 44. Two orifices at two ends of the sealing gasket are formation continuous phase injection orifices 41, orifices adjacent thereto are detection continuous phase injection orifices 42, and then in turn, orifices are formation continuous phase injection orifices 41, in such a way, the formation continuous phase injection orifices 41 and the detection continuous phase injection orifices 42 are symmetrically and alternately arranged at the two ends. The upper ends and the lower ends of the formation continuous phase injection orifice 41 and the detection continuous phase injection orifice 42 are each provided with a first annular seal 43, and the first annular seal 43 is of a single-ring structure or a multi-ring structure.

Figure 2:
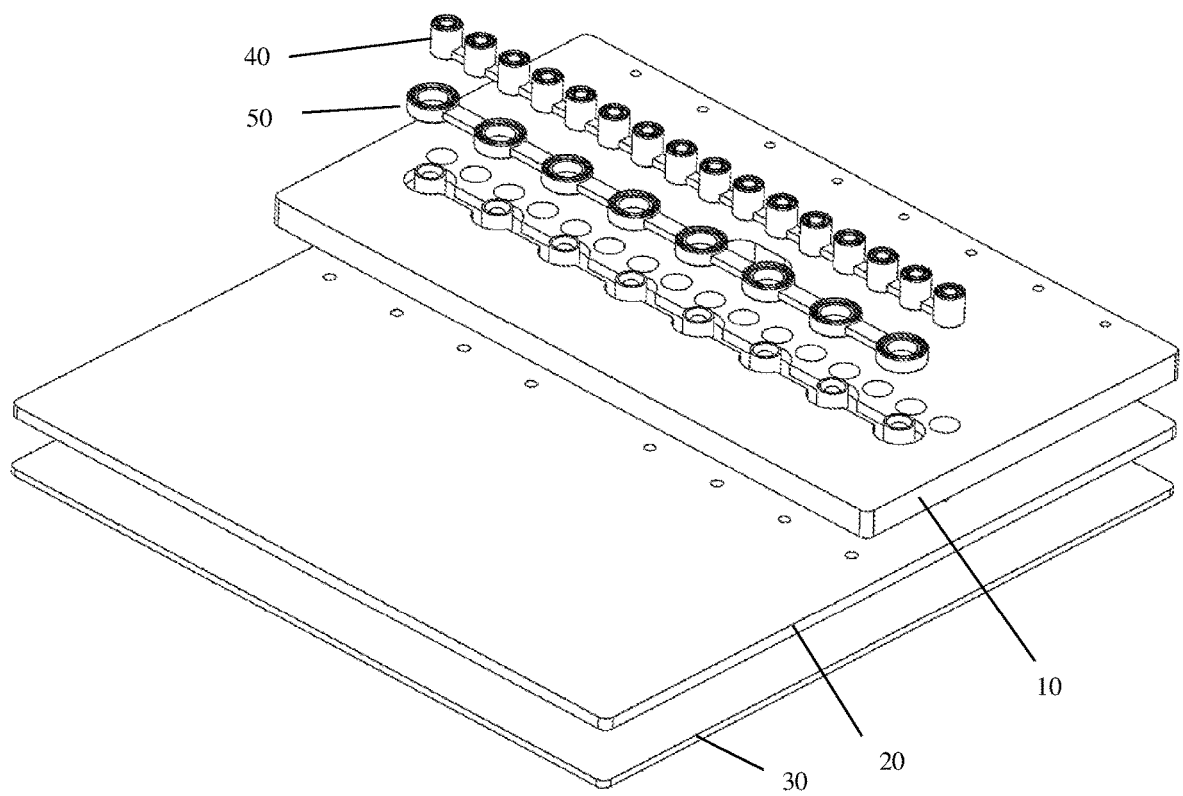
FIG. 2 is a composition schematic diagram of the microfluidic chip in FIG. 1.
Figure 3:
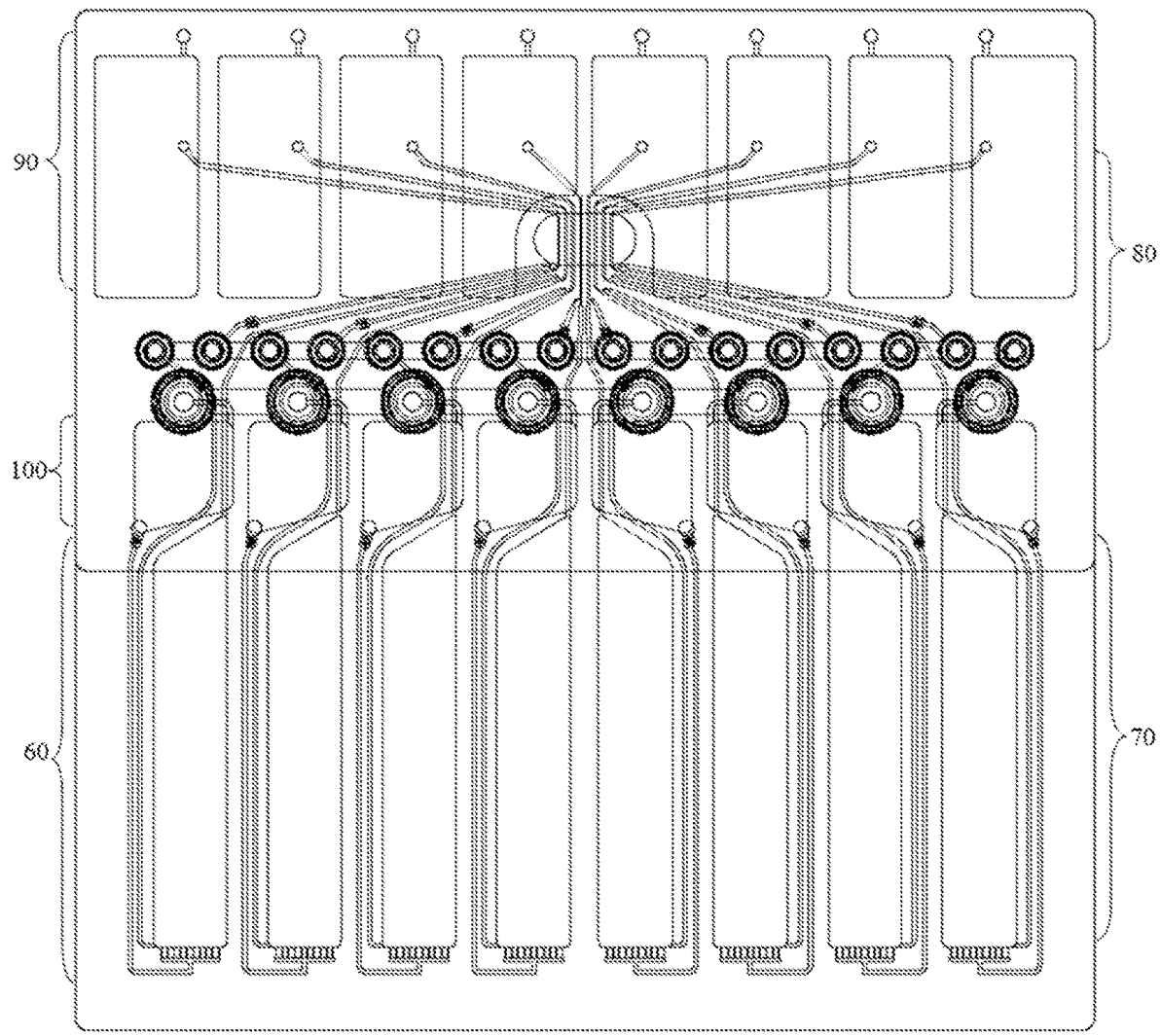
FIG. 3 is a schematic diagram of distribution of functional zones of the microfluidic chip in FIG. 1.
Figure 4:
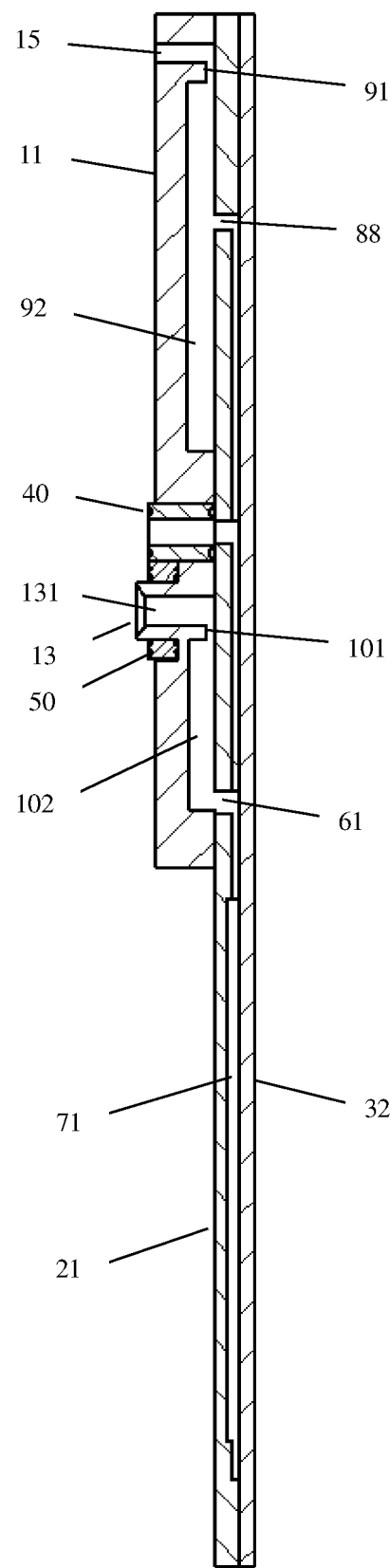
FIG. 4 is a sectional view of the microfluidic chip in FIG. 1.

As shown in FIG. 1 to FIG. 3, the formation continuous phase injection orifice 41 and the detection continuous phase injection orifice 42 are aligned with the formation continuous phase inlet 64 and the detection continuous phase inlet 81, respectively. The waste liquid outlet 88 is aligned and communicates with the waste liquid storage pool 92, and the sample inlet 61 is aligned with the sample outlet 103.

The microfluidic chip is horizontally placed during sample loading, and the sample phase is injected from the sample injection orifice 131 and enters the sample storage pool 102 through the sample loading micro-channel 101. Subsequently, the microfluidic chip is vertically or obliquely placed, with the waste liquid storage zone 90 located at the upper end. For droplet formation, the formation continuous phase is injected from the formation continuous phase injection orifice 41 of the sealing gasket 40, enters the formation continuous phase inlet 64, and then enters the droplet storage pool 71, and the sample phase enters the sample phase inlet 61 through the sample outlet 103 under the action of pressure. For detection, the detection continuous phase is injected from the detection continuous phase injection orifice 42 and enters the detection continuous phase inlet 81.

During detection, the droplet inlet 84 is located at the top of the droplet storage pool 71. When the detection continuous phase enters and fills the droplet storage pool 71, the droplets float up and are pushed by the detection continuous phase to enter the droplet channel 85 through the droplet inlet 84. The tapered sharp-corner-shaped upper end of the droplet storage pool 71 is beneficial for collection of the droplets at the droplet inlet 84 as well as rapid and thorough discharge of the droplets.

The lower end of the sample storage pool 102 is in the oblique shape, and the sample outlet 103 is arranged at the bottom sharp corner of the sample storage pool 102, which is beneficial for the thorough discharge of the sample phase from the sample outlet 103.

Figure 13:
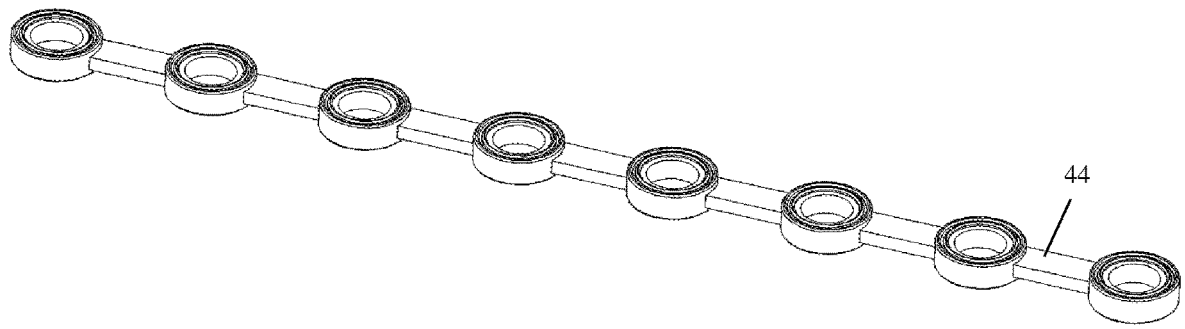
FIG. 13 is a schematic diagram of a sealing ring of the microfluidic chip in FIG. 1.
Figure 14:
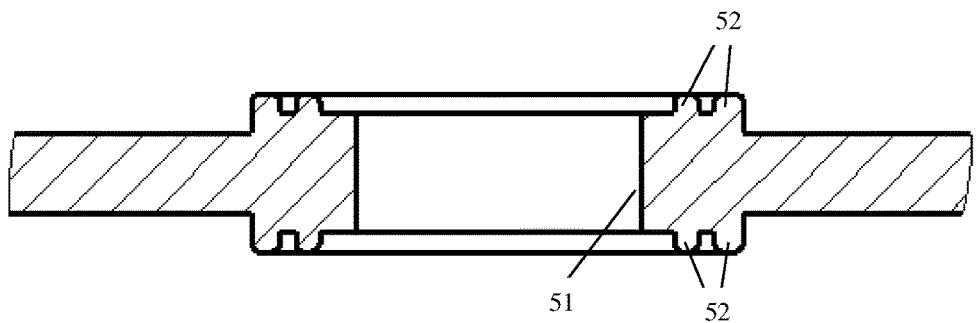
FIG. 14 is a sectional view of the sealing ring of the microfluidic chip in FIG. 1.

As shown in FIG. 13 and FIG. 14, in the embodiment, the sealing ring 50 includes eight circular rings that are connected by means of the connecting sections 44, the upper ends and the lower ends of the circular rings are each provided with a single-ring or multi-ring second annular seal 52, and an inner wall 51 of the circular ring sleeves the sample loading column 13. The thickness of the membrane 30 is less than 1 mm, and the membrane 30 should be as thin as possible to accelerate the heat transfer during the PCR reaction.

The microfluidic chip of the application integrates the whole-process operation steps of droplet digital PCR, such as the sample storage and transfer, the droplet formation, the droplet storage, the PCR thermal cycling and the droplet detection, thereby significantly reducing manual operation, reducing the operation difficulty, meeting the requirement for automatic clinical detection, and being capable of simultaneously processing a plurality of independent samples to obviously improve the detection efficiency.

What is claimed is:

1. A microfluidic chip, comprising a chip upper cover, a chip lower layer, a membrane, a sealing gasket and a sealing ring; wherein a lower surface of the chip upper cover fits to an upper surface of the chip lower layer, and a lower surface of the chip lower layer fits to an upper surface of the membrane;
    the microfluidic chip is provided with a sample storage zone, a droplet formation zone, a droplet storage zone, a droplet detection zone and a waste liquid storage zone, the sample storage zone and the waste liquid storage zone are arranged on the lower surface of the chip upper cover, the droplet formation zone, the droplet storage zone and the droplet detection zone are arranged on the lower surface of the chip lower layer, and communication between the sample storage zone and the droplet formation zone, communication between the droplet formation zone and the droplet storage zone, communication between the droplet storage zone and the droplet detection zone, and communication between the droplet detection zone and the waste liquid storage zone are all realized by means of a micro-channel or a micropore;
    the microfluidic chip is horizontally placed during sample loading; and the microfluidic chip is vertically or obliquely placed during droplet formation, PCR reaction and droplet detection, wherein the droplet formation zone is located at the lower end of the microfluidic chip, and the waste liquid storage zone is located at the upper end of the microfluidic chip;
    wherein the sealing gasket is symmetrically provided with a formation continuous phase injection orifice and a detection continuous phase injection orifice alternately, the formation continuous phase injection orifice is connected with the detection continuous phase injection orifice by means of a connecting section, and the left end and the right end of the sealing gasket are provided with formation continuous phase injection orifices; the upper ends and the lower ends of the formation continuous phase injection orifice and the detection continuous phase injection orifice are each provided with a first annular seal.

2. The microfluidic chip according to claim 1, wherein the chip upper cover is provided with a sample injection orifice, a sealing gasket mounting hole, an exhaust hole and a window penetrating through an upper surface and the lower surface of the chip upper cover; the upper surface of the chip upper cover is provided with a sample loading column, and the sample injection orifice is arranged at the center of the sample loading column; and the lower surface of the chip upper cover is provided with a sample loading micro-channel, a sample storage pool, an exhaust channel and a waste liquid storage pool, wherein the sample injection orifice is connected with the sample storage pool by means of the sample loading micro-channel, and the waste liquid storage pool is connected with the exhaust hole by means of the exhaust channel.

3. The microfluidic chip according to claim 1, wherein
    the sealing ring comprises a circular ring connected by a connecting section, the upper end and the lower end of the circular ring are each provided with a single-ring or multi-ring second annular seal, and an inner wall of the circular ring sleeves the sample loading column; and
    a thickness of the membrane is less than 1 mm.

4. The microfluidic chip according to claim 1, wherein the droplet storage zone is provided with a droplet storage pool, and an upper end of the droplet storage pool is in a shape of sharp corner; the droplet formation zone comprises a formation continuous phase inlet, a formation continuous phase channel communicating with the formation continuous phase inlet, a sample inlet and a sample channel communicating with the sample inlet, wherein, the formation continuous phase inlet communicates with the formation continuous phase injection orifice of the sealing gasket;
    the sample channel is connected with at least one sample branching channel, and the sample branching channel is connected with the droplet storage pool by means of a horn mouth; and
    the formation continuous phase channel is provided with a formation continuous phase filtering zone, and the sample channel is provided with a sample filtering zone.

5. The microfluidic chip according to claim 4, wherein micro-columns are densely arranged at a distance of 10 μm to 100 μm in the sample phase filtering zone and the formation continuous phase filtering zone;
    the horn mouth is a bilaterally symmetrical opening in <shape or a single-bevel opening in ∠ shape, and an angle of the horn mouth ranges from 5 degrees to 120 degrees; and
    a number of the sample phase branching channels preferably ranges from 1 to 40.

6. The microfluidic chip according to claim 5, wherein a depth of the droplet storage pool is greater than or equal to twice a depth of the horn mouth, the depth of the droplet storage pool is greater than or equal to twice a depth of the sample phase branching channel, and the depth of the horn mouth is the same as that of the sample phase branching channel.

7. The microfluidic chip according to claim 6, wherein a width-depth ratio of the sample phase branching channel is greater than or equal to 1, a width of the sample phase branching channel ranges from 10 μm to 200 μm, the depth of the sample phase branching channel ranges from 2 μm to 100 μm, and the depth of the droplet storage pool is greater than 50 μm.

8. The microfluidic chip according to claim 1, wherein the droplet detection zone comprises a detection continuous phase inlet, a detection continuous phase channel communicating with the detection continuous phase inlet, a droplet inlet, a droplet channel communicating with the droplet inlet and a detection channel, wherein,
    the detection continuous phase inlet communicates with the detection continuous phase injection orifice of the sealing gasket;
    the detection continuous phase channel is provided with a detection continuous phase filtering zone, and micro-columns are densely arranged at a distance of 10 μm to 100 μm in the detection continuous phase filtering zone;
    the detection continuous phase channel merges into the droplet channel to connect with the detection channel, the detection channel communicates with a waste liquid channel, and the waste liquid channel is connected with a waste liquid outlet; and
    a width of the detection channel is 1-1.5 times a droplet diameter, and a depth of the detection channel is 1-1.5 times the droplet diameter.

9. The microfluidic chip according to claim 1, wherein the sample storage zone comprises the sample loading micro-channel, the sample storage pool and a sample outlet, and a lower end of the sample storage pool is in an oblique shape; the sample outlet is arranged at the bottom sharp corner of the sample storage pool, and the sample outlet communicates with the sample inlet of the droplet formation zone; and the waste liquid storage zone comprises the exhaust channel and the waste liquid storage pool, and the waste liquid storage pool is connected with the exhaust hole by means of the exhaust channel.

10. The microfluidic chip according to claim 1, wherein the sample phase is preferably aqueous phase, the formation continuous phase and the detection continuous phase are preferably oil phase, and the droplet is preferably a water-in-oil droplet.

11. A microfluidic chip, comprising a chip upper cover, a chip lower layer, a membrane, a sealing gasket and a sealing ring; wherein a lower surface of the chip upper cover fits to an upper surface of the chip lower layer, and a lower surface of the chip lower layer fits to an upper surface of the membrane;
    the microfluidic chip is provided with a sample storage zone, a droplet formation zone, a droplet storage zone, a droplet detection zone and a waste liquid storage zone, the sample storage zone and the waste liquid storage zone are arranged on the lower surface of the chip upper cover, the droplet formation zone, the droplet storage zone and the droplet detection zone are arranged on the lower surface of the chip lower layer, and communication between the sample storage zone and the droplet formation zone, communication between the droplet formation zone and the droplet storage zone, communication between the droplet storage zone and the droplet detection zone, and communication between the droplet detection zone and the waste liquid storage zone are all realized by means of a micro-channel or a micropore;
    the microfluidic chip is horizontally placed during sample loading; the microfluidic chip is vertically or obliquely placed during droplet formation, PCR reaction and droplet detection, wherein the droplet formation zone is located at the lower end of the microfluidic chip, and the waste liquid storage zone is located at the upper end of the microfluidic chip; wherein,
    the chip upper cover is provided with a sample injection orifice, a sealing gasket mounting hole, an exhaust hole and a window penetrating through an upper surface and the lower surface of the chip upper cover; the upper surface of the chip upper cover is provided with a sample loading column, and the sample injection orifice is arranged at the center of the sample loading column; the lower surface of the chip upper cover is provided with a sample loading micro-channel, a sample storage pool, an exhaust channel and a waste liquid storage pool, wherein the sample injection orifice is connected with the sample storage pool by means of the sample loading micro-channel, and the waste liquid storage pool is connected with the exhaust hole by means of the exhaust channel;
    the sealing gasket is symmetrically provided with a formation continuous phase injection orifice and a detection continuous phase injection orifice alternately, the formation continuous phase injection orifice is connected with the detection continuous phase injection orifice by means of a connecting section, and the left end and the right end of the sealing gasket are provided with formation continuous phase injection orifices; the upper ends and the lower ends of the formation continuous phase injection orifice and the detection continuous phase injection orifice are each provided with a first annular seal;
    the sealing ring comprises a circular ring connected by a connecting section, the upper end and the lower end of the circular ring are each provided with a single-ring or multi-ring second annular seal, and an inner wall of the circular ring sleeves the sample loading column;
    a thickness of the membrane is less than 1 mm;
    the droplet storage zone is provided with a droplet storage pool, and an upper end of the droplet storage pool is in a shape of sharp corner; the droplet formation zone comprises a formation continuous phase inlet, a formation continuous phase channel communicating with the formation continuous phase inlet, a sample inlet and a sample channel communicating with the sample inlet, wherein,
    the formation continuous phase inlet communicates with the formation continuous phase injection orifice of the sealing gasket;
    the sample channel is connected with at least one sample branching channel, and the sample branching channel is connected with the droplet storage pool by means of a horn mouth;
    the formation continuous phase channel is provided with a formation continuous phase filtering zone, and the sample channel is provided with a sample filtering zone;
    micro-columns are densely arranged at a distance of 10 μm to 100 μm in the sample phase filtering zone and the formation continuous phase filtering zone;
    the horn mouth is a bilaterally symmetrical opening in < shape or a single-bevel opening in ∠ shape, and an angle of the horn mouth ranges from 5 degrees to 120 degrees;
    a number of the sample phase branching channels preferably ranges from 1 to 40;
    a depth of the droplet storage pool is greater than or equal to twice a depth of the horn mouth, the depth of the droplet storage pool is greater than or equal to twice a depth of the sample phase branching channel, and the depth of the horn mouth is the same as that of the sample phase branching channel;

a width-depth ratio of the sample phase branching channel is greater than or equal to 1, a width of the sample phase branching channel ranges from 10 μm to 200 μm, the depth of the sample phase branching channel ranges from 2 μm to 100 μm, and the depth of the droplet storage pool is greater than 50 μm;

the droplet detection zone comprises a detection continuous phase inlet, a detection continuous phase channel communicating with the detection continuous phase inlet, a droplet inlet, a droplet channel communicating with the droplet inlet and a detection channel, wherein, the detection continuous phase inlet communicates with the detection continuous phase injection orifice of the sealing gasket;

the detection continuous phase channel is provided with a detection continuous phase filtering zone, and micro-columns are densely arranged at a distance of 10 μm to 100 μm in the detection continuous phase filtering zone;

the detection continuous phase channel merges into the droplet channel to connect with the detection channel, the detection channel communicates with a waste liquid channel, and the waste liquid channel is connected with a waste liquid outlet;

a width of the detection channel is 1-1.5 times a droplet diameter, and a depth of the detection channel is 1-1.5 times the droplet diameter;

the sample storage zone comprises the sample loading micro-channel, the sample storage pool and a sample outlet, and a lower end of the sample storage pool is in the oblique shape; the sample outlet is arranged at the bottom sharp corner of the sample storage pool, and the sample outlet communicates with the sample inlet of the droplet formation zone; the waste liquid storage zone comprises the exhaust channel and the waste liquid storage pool, and the waste liquid storage pool is connected with the exhaust hole by means of the exhaust channel; and the sample phase is preferably aqueous phase, the formation continuous phase and the detection continuous phase are preferably oil phase, and the droplet is preferably a water-in-oil droplet.

* * * * *